United States Patent
Thompson et al.

(10) Patent No.: US 6,348,317 B1
(45) Date of Patent: Feb. 19, 2002

(54) FLUORESCENT AND DNA CLEAVAGE PROPERTIES OF PEPTIDE/DYE CONJUGATES

(75) Inventors: Martin Thompson, Scottsdale; Neal W. Woodbury, Tempe, both of AZ (US)

(73) Assignee: The Arizona Board of Regents, Tempe, AZ (US)

( * ) Notice: Subject to any disclaimer, the term of this patent is extended or adjusted under 35 U.S.C. 154(b) by 0 days.

(21) Appl. No.: 09/713,950

(22) Filed: Nov. 16, 2000

Related U.S. Application Data

(60) Provisional application No. 60/166,139, filed on Nov. 18, 1999.

(51) Int. Cl.⁷ .................. C12Q 1/68; G01N 33/53; A61K 38/00; C07K 1/00
(52) U.S. Cl. .................. 435/6; 435/7.1; 530/300; 530/350
(58) Field of Search ............ 435/6, 7.1; 530/300, 530/350

(56) References Cited

U.S. PATENT DOCUMENTS

| | | | | |
|---|---|---|---|---|
| 4,963,658 A | * | 10/1990 | Kung et al. | 530/406 |
| 5,534,424 A | * | 7/1996 | Uhlen et al. | 435/91.2 |
| 5,593,867 A | * | 1/1997 | Walker et al. | 435/91.2 |
| 5,656,426 A | * | 8/1997 | Law et al. | 435/6 |
| 5,830,665 A | * | 11/1998 | Shuber et al. | 435/6 |

OTHER PUBLICATIONS

B.M. Sutherland, et al., "Promoter–Specific Synthetic Photoendonuclease; Rose Bengal–Labeled T7 RNA Polymerase," Biochemistry 32:1788–1794, 1993.

M. Thompson and N.W. Woodbury, "Fluorescent and Photochemical Properties of a Single Zinc Finger Crosslinked with a Fluorescent DNA–binding Probe," ACS Western Regional Meeting, Oct. 6–8, 1999.

M. Thompson and N.W. Woodbury, "Fluorescent and Photochemical Properties of a Single Zinc Finger Conjugated to a Fluorescent DNA–Binding Probe," *Biochemistry* 39(15):4327–4338, 2000.

\* cited by examiner

*Primary Examiner*—Kenneth R. Horlick
(74) *Attorney, Agent, or Firm*—Quarles & Brady LLP

(57) ABSTRACT

A method of identifying the presence or absence of a DNA molecule in a test sample comprising a specific DNA sequence is disclosed. In one embodiment, the method comprises the steps of mixing a test sample with a peptide/dye conjugate comprising a covalently linked peptide and a dye, wherein the peptide binds to the specific DNA sequence and wherein the peptide/dye conjugate will fluoresce if the peptide is bound to the specific DNA sequence, and measuring fluorescence, wherein specific fluorescence above background level indicates that the conjugate is bound to the specific DNA sequence. In another embodiment, the present invention is a method of cleaving a specific DNA molecule and a test sample. The method comprises mixing a test sample with a peptide dye conjugate comprising a covalently linked peptide and a dye, wherein the peptide binds to the specific DNA sequence and wherein the peptide dye conjugate will cleave if the peptide is bound to a specific DNA sequence.

26 Claims, 8 Drawing Sheets

```
GRE1:   5'-TCATACCACTAACTGTTCTATCA-3'
GRE2:   5'-TGATACGGCTGACTGTTCTATGA-3'
GRE3:   5'-TCATACATCTAACTATTCTATCA-3'
                              *
GRE4:   5'-TCATACATCTAACTGTCCTATCA-3'
                               *
ERE5'-  5'-TCATACATCTAACTGACCTATCA-3'
```

```
            202                                                    253
Tc3:  N-[TO]-PRGSALSDTERAQLDVMKLLNVSLHEMSRKISRSRHCIRVYLKDPVSYGTS-C
            139                                                    190
Hin:  N-[YO]-GRPRAINKHEQEQISRLLEKGHPRQQLAIIFGIGVSTLYRYFPASSIKKRMN-C
```

X = O (OXAZOLE YELLOW), OR S (THIAZOLE ORANGE)

```
            202                                                    253
Tc3:  N-[TO]-PRGSALSDTERAQLDVMKLLNVSLHEMSRKISRSRHCIRVYLKDPVSYGTS-C
            139                                                    190
Hin:  N-[YO]-GRPRAINKHEQEQISRLLEKGHPRQQLAIIFGIGVSTLYRYFPASSIKKRMN-C
```

TC3: 5'-ATCGGCACGATGCAGTT<u>CTATAGGACCCC</u>CC-3' hixL: 5'-TC<u>TTATCAAA</u>AACACTATCGTCGCACGGCTAC-3'

NS: 5'-TCCATGCACGTCGACGTACGTCGCACGGCTAC-3'

FIG. 8

FLUORESCENT AND DNA CLEAVAGE PROPERTIES OF PEPTIDE/DYE CONJUGATES

CROSS-REFERENCE TO RELATED APPLICATIONS

This application claims the benefit of U.S. provisional application, Ser. No. 60/166,139, filed on Nov. 18, 1999. This application is incorporated by reference herein.

STATEMENT REGARDING FEDERALLY SPONSORED RESEARCH OR DEVELOPMENT

BACKGROUND OF THE INVENTION

DNA-binding proteins contain domains with small structural motifs designed to discriminate specific DNA sequences through an ensemble of non-covalent interactions. C.O. Pabo, et al., *Ann. Rev. Biochem.* 61:1053–1095 (1992). Positioning of the α-helix in the major groove of DNA is a common motif found in both non-sequence specific and sequence specific DNA binding proteins and yields a defined arrangement of non-covalent contacts between amino acid side chains of the protein and DNA bases and backbone structures. A. J. Doherty, et al., *Nucl. Acids Res.* 24:2488–2497 (1996); A. Revzin, et al., *The Biology of Non-Specific DNA-Protein Interactions* (1990); R. S. Spolar, et al., *Science* 362:777–784 (1994); D. P. Mack, et al., *Biochemistry* 29:6561–6567 (1990). Typically, in protein structural motifs such as the helix-turn-helix ("HTH"), R. G. Brennan, et al., *J. Biol. Chem.* 264:1903–1906 (1989); E. R. P. Zuiderweg, et al., *FEBS* 174:243–247 (1984); E. R. P. Zuiderweg, et al., *Proc. Natl. Acad. Sci. USA* 80:5837–5841 (1983); S. C. Harrison, et al., *Ann. Rev. Biochem.* 59:933–969 (1990), zinc-finger, A. Klug, et al., *Trends Biochem. Sci.* 12:464–469 (1987); J.M. Berg, *Ann. Rev. Biophys. Biophysic. Chem.* 19:405–421 (1990); N. P. Pavletich, et al., *Science* 252:809–817 (1991); J. E. Coleman, *Ann. Rev. Biochem.* 61:897–946 (1992), or leucine zipper, E. K. O'Shea, et al., *Science* 254:539–544 (1991); E. K. O'Shea, et al., *Science* 243:538–542 (1989), the smallest DNA recognition element is an a-helix which binds to the DNA major groove. The remainder of the protein typically contains structural motifs, which orient this recognition element within the major groove, provide non-specific DNA-binding affinity, and enable additional interactions such as dimerization or ligand binding.

Single zinc fingers ("ZF") have been studied for their ability to fold independently and bind native recognition sequences of the wild type protein. B. E. Bernstein, et al., *Biochemistry* 33:4460–4470 (1994); A. D. Frankel et al., *Proc. Natl. Acad. Sci. USA* 84:4841–4845 (1987); B. A. Krizek, et al., *J. Am. Chem. Soc.* 113:4518–4523 (1991); M. S. Lee, et al., *Science* 245:635–637 (1989). Most proteins that recognize particular DNA sequences via zinc finger motifs have multiple zinc fingers in the DNA-binding domain ("DBD"). J. Miller, et al., *EMBO J.* 4:1609–1614 (1985). The contribution to sequence recognition of each zinc finger within the DNA binding domain of a protein can vary significantly. D. J. Whyatt, et al., *EMBO J.* 12:4993–5005 (1987). For example, in the glucocorticoid and estrogen receptor DNA-binding domains, the N-terminal finger contains all the interactions for sequence specificity, whereas the C-terminal zinc finger further stabilizes DNA binding by interacting non-specifically. Finger swapping studies, in which the N- and C-terminal zinc fingers of the estrogen receptor ("ER") and glucocorticoid receptor ("GR") where switched, clearly show that sequence recognition was a function of the N-terminal zinc finger. S. Green, et al., *Nature* 325:75–78 (1987).

These studies have made it possible to produce short (less than 50 amino acid) single zinc finger peptides that bind to specific DNA sequences with moderately high affinity. T. K. Archer, et al., *Proc. Natl. Acad. Sci. USA* 87:7560–7564 (1990). Thus, it is possible to synthetically generate peptides that bind under normal physiological conditions to specific DNA sequences, N. Y. Sardesai, et al., *J. Biol. Inorg. Chem.* 2:762–771 (1997); M. G. Oakley, et al., *Biocon. Chem.* 5:242–247 (1994); J. A. Shin, et al., *Nucl. Acids Res.* 19:5233–5236 (1991); K. S. Graham, et al., *J. Biol. Chem.* 265:16534–16540 (1990); M. G. Oakley, et al., *Science* 248:847–850 (1990); J. P. Sluka, et al., *Science* 238:1129–1132 (1987), opening the door for the production of a variety of different types of chemical reagents, which probe or modify DNA at specific sequences.

SUMMARY OF THE INVENTION

In one embodiment, the present invention is a method of identifying the presence or absence of a DNA molecule that contains a specific DNA sequence. The method comprises the steps of mixing a test sample with a peptide/dye conjugate comprising a covalently linked peptide and a cyanine dye wherein this peptide binds to a specific DNA sequence and wherein the peptide/dye conjugate will significantly fluoresce if the peptide is bound to a specific DNA sequence and measuring fluorescence, wherein specific fluorescence of above background level indicates that the conjugate is bound to the specific DNA sequence.

In a preferred form of the present invention, the dye is an intercalating dye and selected from the group of cyanine dyes.

In a particularly advantageous form of the invention, the dye is chosen from thiazole orange and oxazole yellow.

In another embodiment, the present invention is a method of cleaving a DNA molecule, wherein the DNA molecule comprises a specific DNA sequence. The method comprises the steps of mixing a test sample with a peptide/dye conjugate comprising a covalently linked peptide and a dye, wherein the peptide/dye is bound to the specific DNA sequence and wherein the peptide/dye conjugate will cleave the DNA if bound and if one applies a triggering event. One then applies the trigger event and the specific DNA sequence is cleaved.

In a preferred form of this embodiment, the triggering event is the administration if light.

In another embodiment, the present invention is a composition comprising a dye and a peptide, wherein the peptide binds to a specific DNA sequence and the dye is capable of fluorescence only when the conjugate is bound to a specific DNA sequence.

In another embodiment, the present invention is a composition comprising a covalently linked dye and peptide, wherein the peptide binds to a specific DNA sequence and the dye is capable of cleavage only when the conjugate is bound to a specific DNA sequence and only in the presence of a triggering event.

It is an object of the present invention to detect specific DNA sequences.

It is another object of the present invention to cleave specific DNA sequences.

It is another object of the present invention to provide a peptide/dye conjugate.

BRIEF DESCRIPTION OF THE DRAWINGS

FIG. 8 is a list of the three 40 base oligonucleotide sequences used in these studies. The native consensus sequences for the Tc3 transposase (Tc3) and the Hin recombinase (hixL) DNA-binding domains are underlined.

DESCRIPTION OF THE INVENTION

1. In General

Figures 1, 2:
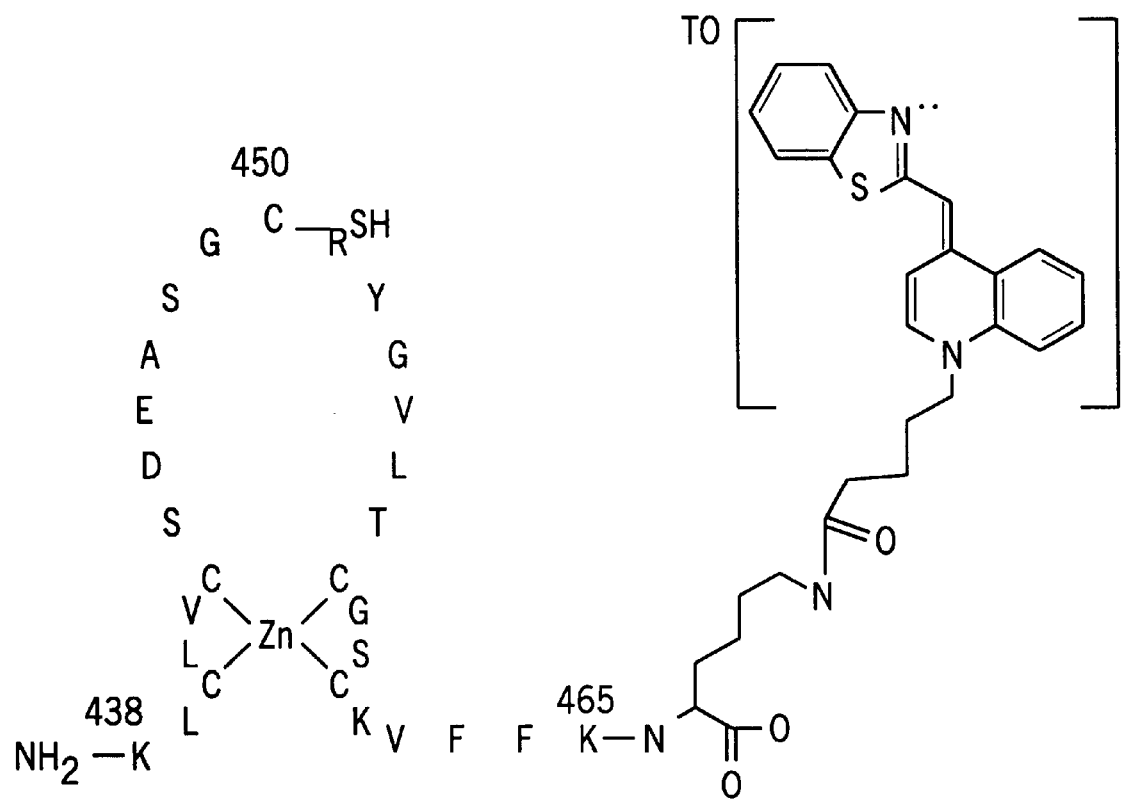
FIG. 1 is a schematic representation of the thiazole orange-zinc finger (TO-ZF) conjugate.
FIG. 2 is a list of the 23 base oligomers used throughout these experiments. The native GRE target sequence is underlined. Base changes in the hexameric GRE half-site are indicated by an asterisk.

In one embodiment, the present invention is the combination of the sequence-specific binding properties of oligopeptides with the DNA-specific fluorescence properties or cleavage properties of intercalating dyes and other light-absorbing molecules. We investigated whether a peptide/dye conjugate can be made wherein the conjugate retains the peptide's DNA sequence recognition and binding specificity and the dye in the conjugate fluoresces upon conjugate's binding to the specific DNA's sequence. We theorized that if such a conjugate can be made, it will provide a new way for detecting specific DNA sequences.

The Examples below disclose three conjugates, each comprising a peptide and a cyanine dye, that have been made by covalently linking the cyanine dye to the peptide. The three conjugates are GR-DBD zinc finger/thiazole orange ("TO-ZF"), Tc3 transposase-DBD HTH/thiazole orange ("Tc3TO"), and Hin recombinase-DBD HTH/oxazole yellow ("HinYO"). All three conjugates have been shown to be able to recognize and bind to their peptides' respective native consensus DNA sequence. All three conjugates have been shown to be able to fluoresce beyond background level upon binding to their respective specific DNA sequence. When the DNA cleavage activity was tested with TO-ZF, the TO-ZF conjugate was able to cleave the DNA upon visible light exposure. Because the DNA cleavage activity of the conjugate came from the cyanine dye and both TO and YO can cleave DNA upon visible light exposure, it is expected that Tc3TO and HinYO are able to cleave their respective specific DNA sequence in a similar fashion as TO-ZF upon visible light exposure. The DNA sequence specificity, when tested with the TO-ZF conjugate as shown in the example below, reproduced features of response element recognition found in the native glucocorticoid receptor.

Thus, these conjugates such as TO-ZF can work (fluoresce and cleave DNA) under physiological conditions.

2. Suitable Peptides/Dye Conjugates

The peptide/dye conjugates that can be built to provide fluorescence and cleavage capabilities upon binding to a specific DNA sequence are not limited to the three Examples described below and above. Any peptide that recognizes and binds to a specific DNA sequence can be used to make such a conjugate, as long as the peptide can either be synthesized using solid phase synthesis methods or expressed from an engineered gene in such a way that a specific dye attachment site (for example a unique cysteine or lysine) is available.

The amino-terminal zinc finger of the glucocorticoid receptor DNA binding domain ("GR-DBD") is a candidate for the protein part of such a peptide/dye conjugates. GR is a protein containing two non-putative zinc finger motifs in its DNA binding domain. B. F. Luisi, et al., *Nature* 352:497–505 (1991); M. A. A. v. Tilborg, et al., *J. Molec. Biol.* 247:689–700 (1995). The protein has been thoroughly characterized, both biochemically and structurally, and its DNA binding interactions are known in atomic detail. B. F. Luisi, et al., supra, 1991.

Other suitable examples of the peptide candidate for the peptide/dye conjugates of the present invention include, among other, the HTH motifs from Hin recombinase and Tc3 transposase.

Tc3 of C. elegans is a member of the Tc1/mariner family of transposable elements. Transposable elements (transposons) are small stretches of DNA that can move from one position in the genome to another. R. H. A. Plasterk, *Curr. Topics Microbiol. Immunol.* 204:125–143 (1996). The protein responsible for excision and insertion of the transposon into the genome, called transposases, are encoded by the transposon sequences. In this particular family of transposons, only a single protein, the transposase, is encoded by this gene and is capable of performing the entire transposition reaction in vitro. D. Lampe, et al., *EMBO J.* 15:5470–5479 (1996); J. C. Vos, et al., *Genes Dev.* 10:755–761 (1996). Crystal structure data, van G. Pouderoyen, et al., *EMBO J.* 16:6044–6054 (1997), of the HTH motif shows hat the N-terminal end of the 52 residue fragment comprising the DNA-binding domain of Tc3 transposase is oriented in the minor groove. This further stabilizes the binding interaction by acting as a "thumb" to grip the DNA.

Hin recombinase of *S. typhimurium* belongs to the class of DNA-cleaving enzymes known as invertases or recombinases. Hin catalyzes a DNA inversion reaction of a 1-kb segment of the chromosome to control alternate expression of two flagellin genes by switching the orientation of the promoter. K. T. Hughes, et al., *EMBO J.* 11:2695–2705 (1992). The Hin proteins recognize and bind to left (hixL) and right (hixR) sites that flank the invertible segment. A specific DNA-protein complex is formed by the Hin recombinase dimers in the presence of a recombinational enhancer sequence and Fis proteins, which interact directly with the enhancer element. This higher order complex is necessary for strand exchange at the hix sites because after recombination, DNA supercoils are lost, providing energy for the reaction. Crystal structure data of the HTH motif of the Hin protein shows that the N- and possibly the C-terminal ends of the 52 residue fragment comprising the DNA-binding domain of Hin recombinase are oriented in the minor groove. J.-A. Feng, et al., *Science* 263:348–355 (1994). The critical sequence specific contacts between the Hin monomer and a hix half-site are an AT base pair that the protein contacts in both the major and minor groove. This facilitates opening of the DNA duplex, exposing bases to solvent.

Previous studies using peptide-probe conjugates, P. B. Dervan, et al., *Tetrahedron* 40:457–465 (1984); N. Y. Sardesai, et al., supra, 1997; J. P. Sluka, et al., supra, 1987, show that the HTH motifs from Hin recombinase and Tc3 transposase retain the ability to recognize the native consensus sequence. These two DNA-binding domains are similar in structure and mode of sequence specific DNA interaction. The HTH motif gets its name from a common region of high secondary structure similarity, consisting of a recognition helix, which spans the major groove and exhibits the majority of sequence specific contacts. A second helix stabilizes the folded structure by forming a hydrophobic pocket and often confers some additional binding stabilization. The HTH motif is found in a wide range of proteins, such as homeodomains, C. O. Pabo, et al., supra, 1992, and transcription factors, D. S. Latchman, *Biochem. J.* 270:281–289 (1990); C. O. Pabo, et al., *Nature* 298:443447 (1982). These motifs recognize a wide range of short DNA sequences, often with submicromolar binding constants. M. F. Bruist, et al., *Science* 235:777–780 (1987).

Both Tc3 and Hin recognize their cognate sequence via an HTH motif containing a single recognition helix, both DNA-binding domains are from enzymes that recognize and cleave DNA and both allow specific placement of the fluorophore at a position far enough from the bound protein such that adverse affects of dye intercalation on DNA structure should be minimized, H. Spielmann, et al., *Biochemistry* 34:8542–8553 (1995). In spite of the lack of sequence homology (FIG. 1), the similarity in secondary structure suggests that these two DNA-binding domains will exhibit similar modes of DNA binding. The recognition helix, common in the HTH motif, orients itself within the major groove while two smaller helices stabilize the binding event by interacting nonspecifically with the backbone and stabilizing the structure of the DNA-binding domain by forming a hydrophobic core. Both of these DNA-binding domains also have a short length of their C- and N-termini that stabilize binding by forming specific interactions in the minor groove.

Dyes that fluoresces beyond background fluorescence level when intercalated in DNA are preferred in the present invention. Most preferable dyes for the present invention are DNA intercalating dyes. The dyes come in three basic chemical forms that are useful for the present invention: cyanine dyes, phenanthridine dyes and acridine dyes. All of these are DNA intercalating dyes and, thus, have the property that the fluorescence increases dramatically upon intercalation into DNA. The dyes do not significantly fluoresce free in solution.

A very large selection can be found in commercial catalogs and websites that provide DNA staining dyes.

The distinguishing characteristic of the dyes that are suitable for this purpose is that their fluorescence increases dramatically upon binding to DNA.

When such a dye is used, the conjugate will fluoresce beyond background level upon binding to a specific DNA sequence. There are a number of intercalating dyes which fluoresce almost exclusively when intercalated in DNA. (See, for example, R. P. Haugland, in *Handbook of Fluorescent Probes and Research Chemicals*, 144–156, 1996; A. N. Glazer, et al., *Nature* 359:859–861, 1992, both incorporated herein by reference.) As far as selecting dyes for probes, one simply wants dyes that have a large enhancement of fluorescence upon binding to DNA. Beyond that critical parameters are the photo and chemical stability, the wavelength region of excitation (which one might want to match to one's instrumentation), and the availability or ease of synthesis. Candidates for the dye part of peptide/dye conjugates include, among others, thiazole orange ("TO") and oxazole yellow ("YO").

Any dye that can cleave a DNA molecule in which it is intercalated, whether a trigger event such as visible light exposure is required or not, can be used in another embodiment of the invention. When such a dye is used, the conjugate can cleave the DNA to which it binds. Any dye that, when intercalated in DNA, can both fluoresce beyond background level and cleave DNA with or without a triggering event can be used. When such a dye is used, the conjugate can both fluoresce and cleave DNA upon binding to a specific DNA sequence.

Therefore, another potentially attractive feature of the present invention is the ability of a number of dye molecules to cleave DNA in the presence of light. (See, for example, B. Armitage, *Chem. Rev.* 98:1171–1200, 1998; B. Akerman, *Nucl. Acids Res.* 24:1080–1090, 1996, incorporated herein by reference). Any intercalating dye with absorbance in the UV to visible range will cleave DNA to some extent when excited by light. Other dyes share this property. This predominantly occurs via guanine oxidation by the excited state of the dye. The most well-described examples of intercalating molecules that cleave DNA in the presence of UV to visible light are the anthraquinones.

A number of these molecules do not fluoresce very efficiently. This particular embodiment would be good candidates for a system in which one wished to cleave DNA but not necessarily detect it via fluorescence.

NMR studies of the binding of free TO to DNA show that the dye forms base stacking interactions with the purine and pyrimidine bases of DNA. J. P. Jacobsen, et al., *Nucl. Acids Res.* 23:753–760 (1995); L. F. Hansen, et al., *Nucl. Acids Res.* 24:859–867 (1996); H. Spielmann, et al., supra, 1995. TO has a large emission enhancement upon dsDNA intercalation, binds DNA with moderate affinity ($K_d \sim 10^{-5}$M) and is relatively sequence neutral in its DNA recognition. R. P. Haugland, supra, 1996; T. L. Netzel, et al., *J. Phys. Chem.* 99:17936–17947 (1995).

In addition to its established role as a nucleic acid stain, TO has been shown to photocleave dsDNA. B. Akerman, supra, 1996. This should make it possible to assay the specificity and yield of protein directed photocleavage. The ability of the cyanine dye intercalators to cleave DNA upon photoactivation furthermore provides a convenient assay for determining the preferred binding site of the designed complex.

Therefore, the present invention also includes dye/peptide conjugates wherein the dye is designed to cleave DNA when the DNA sequence is bound to the dye/peptide conjugate. This cleavage will typically be in the presence of a light in the UV to visible range.

The present invention includes a peptide/dye conjugates that can bind to a specific DNA sequence and (1) fluoresce beyond background level, (2) cleave DNA with or without a triggering event, or (3) do both.

By proper selection of peptide and dye, it is possible to produce mixtures of photo-cleavers where individual cleavage agents may be activated by different specific wavelengths of light. This aspect of the invention will be useful in the automation of DNA mapping and analysis and in deactivating certain genes.

In the specific example described below, thiazole orange is covalently linked the peptide through a peptide linkage (an amide formed between a carboxylic acid group on the dye molecule and the epsilon amino group of a lysine on the peptide). Conjugates of the present inventions are not limited to this linkage. Any covalent linkage method can be used to covalently link the dye to the peptide.

3. Preferred Methods of the Present Invention

In one embodiment, the present invention can be used to detect the presence of a specific DNA sequence. A peptide that can bind to the specific DNA sequence is linked to a dye that fluoresces when intercalated in DNA. The peptide/dye conjugate is added to a sample comprising the specific DNA sequences under a condition that allows the peptide to bind to the specific DNA. A fluorescence over the background level will indicate the presence of the DNA sequence of interest. When it is desirable to detect a DNA sequence of interest that the peptide in the peptide/dye conjugate does not specifically recognize, a specific DNA sequence that the peptide does recognize can be linked to or inserted into the DNA sequence of interest to allow detection of the DNA sequence of interest by the peptide/dye conjugate.

The present invention can also be used to discover DNA sequences that a specific peptide or a domain of a protein can recognize and bind to.

The peptide/dye conjugate described above can be added to an array of different known DNA sequences under a condition that allows peptide-DNA binding. A fluorescence over background level with any DNA sequence suggests that the peptide can recognize and bind to that DNA sequence.

The present invention can also be used to discover peptides that can bind to a specific DNA sequence. A dye that fluoresces when intercalated in DNA can be linked to many different peptides. (For example, one could use a peptide library.) The specific DNA sequence can be added to an array of these peptide/dye conjugates under a condition that allows peptide-DNA binding. A fluorescence over background level of a peptide/dye conjugate suggests that the peptide can bind to the specific DNA.

The present invention can also be used to detect protein-protein interaction between a protein that can bind to DNA and other proteins or peptides. For example, a dye that fluoresces when intercalated in DNA can be linked to many different peptides. A protein with a piece of DNA bound to it can be added to an array of these peptide/dye conjugates. A fluorescence over background level of a peptide/dye conjugate suggests that the peptide and the protein can interact with each other.

The present invention can also be used to cleave a specific DNA sequence. A dye or other light absorbing molecule that can cleave DNA in the presence of light can be linked to a peptide that can bind to the specific DNA sequence. The DNA sequence can be cleaved by binding the peptide/dye conjugate and supplying the trigger event. When it is desirable to first detect the presence of a specific DNA sequence and then cleave the DNA, a dye that fluoresces when intercalated in DNA and then cleaves DNA when a triggering event occurs can be used to make the peptide/dye conjugate. Low light levels can be used for fluorescence detection and then high light levels for cleavage. The DNA sequence can then be detected and cleaved by binding the peptide/dye conjugate to it.

EXAMPLE 1—TO-ZF CONJUGATE

Methods

Materials. Lepidine, 5-bromovaleric acid, 3-methylbenzothiazole-2-thione, iodomethane, anhydrous ethanol, and triethylamine were purchased from Aldrich and used without further purification. F-moc amino acids and peptide synthesis reagents were purchased from Advanced Chemtech. The F-moc-Lys (Mtt)-OH was purchased from Anaspec. T4 polynucleotide kinase was from Promega and [$\gamma$-$^{32}$P]dATP was purchased from Amersham Pharmacia Biotech.

Instrumentation. $^1$H NMR spectra were recorded on a Varian 300 MHz spectrometer. Peptides were synthesized on a Millipore 9050 peptide synthesizer. Purification of synthetic peptides was performed on an HPLC. Absorbance measurements were made on a Cary V spectrophotometer. Steady-state fluorescence polarization measurements were performed on PTI QuantaMaster QM-1. DNA sequencing gels were run on a Bio-Rad Sequi-Gen GT Sequencing Cell and analyzed on a Molecular Dynamics Storm-840 gel scanner.

Synthesis of 1-(4-Carboxybutyl)-4-(3-methyl-2,3-dihydro-(benzo-1,3-thiazole)-2-methylidene)-quinolinium bromide (Scheme 1). The synthesis of the carboxylic acid derivative of thiazole orange was adapted from published procedures, L. G. S. Brooker, et al., *J. Am. Chem. Soc.* 64:199–210 (1942); H. S. Rye, et al., *Nucl. Acids Res.* 20:2803–2812 (1992). 5.7 g (32 mmol) of 5-bromovaleric acid and 1.5 mL (11 mmol) of lepidine were refluxed in 30 mL of distilled dioxane under nitrogen overnight. The reaction mixture was allowed to cool to room temperature and filtered. The precipitate was washed twice with 10 mL of dioxane followed by 50 mL of petroleum ether to yield 2.6 g (70%) of pure 1-(4-Carboxybutyl)-4-methyl-1,4-dihydro-quinolinium bromide.

2.0 g (11 mmol) of 3-methylbenzothiazole-2-thione and 3.5 mL (55 mmol) of iodomethane were refluxed in 50 mL of absolute ethanol for 4 hours. Diethyl ether was added to the cooled mixture to precipitate the product. Recrystallization from ethanol:diethyl ether gave 3.2 g (90%) of pure 2-methylmercapto-3-methylbenzothiazole iodide.

1.0 g (3 mmol) of 1-(4-Carboxybutyl)-4-methyl-1,4-dihydro-quinolinium bromide and 1.0 g (3 mmol) of 2-methylmercapto-3-methylbenzothiazole iodide were solubilized in 30 mL of absolute ethanol with slight heating for 5 minutes. To this solution, 840 mL (6 mmol) of triethylamine was added causing the reaction mixture to immediately turn a deep red color. Heating was discontinued and the reaction allowed to stir for 60 minutes. Product was precipitated by addition of 150 mL of diethyl ether. Recrystallization from acetone:diethyl ether gave 1.4 g (80% yield) of pure 1-(4-Carboxybutyl)4-(3-methyl-2,3-dihydro-(benzo-1, 3-thiazole)-2-methylidene)-quinolinium bromide. Product characterization for each reaction was performed by thin layer chromatography using EtOAc:AcOH:$H_2O$ (1:2:2, v/v) as the solvent, MALDI-TOF Mass Spectrometry and $^1H$ NMR. MALDI-TOF m/z 391.8 (391.5, calculated for $C_{23}H_{23}N_2O_2S^+$).

Peptide/Conjugate Synthesis, Purification and Characterization. The peptides were synthesized on PAL-PEG-PS resin by automated solid-phase peptide synthesis using F-moc chemistry. S. B. H. Kent, *Ann. Rev. Biochem.* 57:957–989 (1988). The thiazole orange labeled and unlabeled peptides were synthesized individually on the solid support. In the case of the thiazole orange labeled peptide, the first amino acid coupled to the resin was an F-moc-Lys (Mtt)-OH. The Mtt protective group is selectively removed from the e-amine of the lysine by 1% trifluoroacetic acid (TFA) in dichloromethane. A. Aletras, et al., Internat. *J. Pep. Prot. Res.* 45:488–496 (1995). 1-(4-Carboxybutyl)4-(3-methyl-2, 3-dihydro-(benzo-1,3-thiazole)-2-methylidene)-quinolinium was coupled to the e-amine of the lysine using O-(7-azabenzotriazol-1 -yl)-N,N,N',N',-tetramethyluronium hexafluorophosphate (HATU) activated coupling chemistry. After dye coupling, peptide synthesis proceeded under standard conditions. The peptides were removed from the resin and deprotected by TFA cleavage methods for 4 hours. Thiazole orange is stable to standard deprotection and cleavage conditions.

The peptides were purified by RP-HPLC on a Zorbax $C_8$ column (9.4 mm×25 cm) using a water (0.1% TFA)—acetonitrile (0.1% TFA) gradient. Identities of the peptides were confirmed by amino acid analysis and matrix-assisted laser desorption ionization-time of flight (MALDI-TOF). Quantitation of free thiols was performed with 5,5'-Dithiobis (2-nitrobenzoic acid) using L-cysteine as a reference. G. L. Ellman, *Arch. Biochem. Biophys.* 82:70–77 (1996). Peptide quantitation was performed using the Bradford Assay with a BSA reference. M. M. Bradford, *Analyt. Biochem.* 72:248–254 (1976).

Fluorescence Measurements. Steady state fluorescence anisotropy measurements were carried out in 20 mM Tris (pH 7.9), 30 mM NaCl, 20 mM KCl, 1 mM $MgCl_2$, and 5% glycerol. The thiazole orange zinc finger conjugate (TO-ZF) or the zinc finger peptide (ZF) samples were prepared fresh by pre-incubating with $ZnCl_2$ on ice for 30 minutes. DNA samples used were either the non-labeled sequences shown in FIG. 2 or a fluorescein labeled duplex with a sequence matching GRE2 (FIG. 2).

For non-labeled DNA titrations (measuring the fluorescence from thiazole orange), the excitation wavelength was 510 nm and the emission was recorded at 535 nm with a 1.0 nm slit width. Glass cuvettes were used with a 0.3 cm path length. Titrations were performed using a constant concentration of unconjugated thiazole orange (TO) or TO-ZF and titrated with DNA as indicated.

For fluorescein labeled DNA measurements, the excitation wavelength was 491 nm and the emission was recorded at 521 nm with a 1.0 nm slit width. Titrations were performed holding the concentration of fluorescein-labeled DNA constant and increasing the concentration of TO, ZF or TO-ZF as indicated. To correct for the small amount of background fluorescence from TO in these measurements, control experiments were performed in parallel using DNA that was not fluorescein labeled, but was otherwise identical to the labeled DNA fragments. The thiazole orange fluorescence intensity measured in the control experiments was subtracted from the total fluorescence intensity for each data point. Under the excitation conditions of these measurements, the contribution to fluorescence by TO at 521 nm was less than 5% of the maximum fluorescence signal observed in the experiment. Even at the point in the titration where the maximum quenching of fluorescein fluorescence was observed (the point of lowest total fluorescence in the measurement), less than half of the fluorescence was due to TO, and this could accurately be removed by subtraction of the control value. Each point is an average of 60 measurements, and each titration was performed independently three times.

Anisotropy is calculated as: $r=(I_{vv}-gI_{vh})/(I_{vv}+2gI_{vh})$ where, $I_{vv}$ is the fluorescence intensity with vertically polarized excitation and vertically polarized emission, $I_{vh}$ is the fluorescence intensity with vertically polarized excitation and horizontally polarized emission, and g ($I_{hv}/I_{hh}$) is a factor correcting for the polarization dependence of the spectrometer. A two-state binding model was used for the analysis of zinc finger binding to F-GRE2. The data were fitted to equation 1 using nonlinear least squares algorithm.

Here, [GRE]T and [ZF]T are the total concentrations as 50 nM F-GRE2 was titrated with the zinc finger. The parameters of the fit were the anisotropies of the free and bound DNA (AF and AB) and the dissociation constant (Kd).

$$A = A_F + (A_B - A_F)\left[\frac{\left(1 + \frac{[P]_T}{K_d} + \frac{[D]_T}{K_d}\right) - \sqrt{\left(1 + \frac{[P]_T}{K_d} + \frac{[D]_T}{K_d}\right)^2 - \left(4[P]_T[D]_T\left(\frac{1}{K_d}\right)^2\right)}}{2\left(\frac{[P]_T}{K_d}\right)}\right]$$

Total fluorescence data were collected in parallel to the anisotropy measurements and were calculated from raw data as the fluorescence intensity in the vertical plane plus two times the fluorescence intensity of the horizontal plane, ($TF=I_{vv}+2I_{vh}$). These values were used to determine the percent of the maximum fluorescence for each point along the titration and fit to equation 2.

$$f = \frac{(K_d + [C]_T + [D]_T) - \sqrt{(K_d + [C]_T + [D]_T)^2 - (4[C]_T[D]_T)}}{2[C]_T}$$

In equation 2, f corresponds to the fraction of TO-ZF conjugate bound at a given concentration of DNA. The concentration given as [TO(ZF)]T corresponds to either the unconjugated thiazole orange or the TOZF conjugate as indicated and [GRE]T is the total concentration of GRE binding sites. The parameter of the fit was the dissociation constant (Kd).

DNA Synthesis, Footprinting and Photocleavage Experiments. All oligonucleotides were synthesized on a DNA synthesizer using phosphoramidite chemistry, Caruthers, M. H., et al., *Methods in Enzymology* (1987), and purified on a 15% denaturing polyacrylamide gel. Bands were cut out and recovered by soaking the crushed gel pieces in 100 mM Tris, (pH 8.0) 100 mM NaCl buffer for 4–6 hours. Extractions were combined and the urea and salts removed by spin filtration. Oligos were $5'$-$^{32}$P-end-labeled by reaction with [y$^{-32}$P]dATP and T4 polynucleotide kinase at 37° C. for 4 hours. Samples were heat denatured and spin filtered to remove unincorporated [y$^{-32}$P]dATP. Each $5'$-$^{32}$P-end-labeled oligo was annealed with a 2-fold excess of its unlabeled complement. The three 23-base GRE containing oligonucleotides used in this study are shown in FIG. 2.

The protocol for radical hydroxyl footprinting reactions was adapted from previously established methods, A. Revzin, Ed., *Separation, Detection and Characterization of Biological Macromolecules* (1993); P. E. Nielsen, *J. Molec. Recog.* 3:1–25 (1990). Reaction samples comprised of the TO-ZF and $5'$-$^{32}$P-end-labeled GRE2 in 20 mM Tris (pH 7.9), 40 mM NaCl, 20 mM KCl, 1 mM MgCl2 were allowed to equilibrate in the dark at room temperature for 60 minutes. Equal volumes of a freshly prepared solution of 0.2 mM [Fe(EDTA)]$^{2-}$ was mixed with a 0.3% $H_2O_2$ solution and a 10 mM sodium ascorbate solution and added to the reaction sample. After a one minute incubation, the reactions were quenched with an aqueous solution of 20 mM thiourea and 10 mg/ml tRNA. The footprinting reactions were analyzed on a 15% denaturing polyacrylamide gel.

The purified DNA strands shown in FIG. 2 were $5'$-$^{32}$P-end-labeled using T4 polynucleotide kinase and purified as described above. Oxygen removal was performed by bubbling argon through the samples. Irradiations were performed on 100 mL samples in a 1.0 mL glass cuvette fit with a septum using an argon-ion laser at 514 nm with a power of 300 mW/cm$^2$. After irradiation, samples were divided in half and one portion treated with piperidine, the other immediately frozen. Piperidine treatment consisted of adding an equal volume of freshly prepared 20% piperidine in water to the sample followed by heating at 90° C. for 30 minutes. Both the treated and untreated fractions were dried under vacuum. To each dried sample was added 20 mL of 80% formamide in water. The products of the photocleavage experiments were analyzed on a 15% polyacrylamide (19:1) vertical sequencing gel with dimensions 21 cm×40 cm×0.4 mm. Maxam-Gilbert A+G and C+T sequencing reactions were used as a reference. A. M. Maxam, et al., *Meth. Enzymol.* 65:499–560 (1980). Gels were run at 2000V for 1.5–2 hours. Gels were dried and exposed to a phosphorimaging screen for 4 hours and analyzed on a Molecular Dynamics Storm-840 gel scanner in phosphorimaging mode.

Results

Characterization of thiazole orange/zinc finger conjugate. As illustrated in FIG. 1, the 29 amino acid single zinc finger tethered to the dye was derived from residues 438–465 of the native glucocorticoid receptor protein (GR). In FIG. 1, the residues in bold are the ones that make direct contacts with the native glucocorticoid response element (GRE) in the wild type GR. B. F. Luisi, et al., supra, 1991. The purified 29 amino acid TO-ZF thiazole orange peptide conjugate was characterized using matrix-assisted laser desorption ionization-time of flight (MALDI-TOF) mass spectrometry. The expected mass of TO-ZF is 3501.8 and a sharp peak in its mass spectrum is observed for the singly charged species at (m/e)=3501.9. By comparison, the expected mass of the zinc finger itself is 3154.2 and a sharp peak in its spectrum is observed for the singly charged species at (m/e)=3155.6.

The conjugate was further characterized by reversed phase HPLC and UV-Visible absorption. An HPLC analysis of purified TO-ZF shows only one peak in the HPLC chromatograph, which confirms the purity of the preparation. The UV-visible absorbance spectrum of HPLC purified TO-ZF display the additive spectral properties of thiazole orange and the isolated peptide.

Figure 3A:
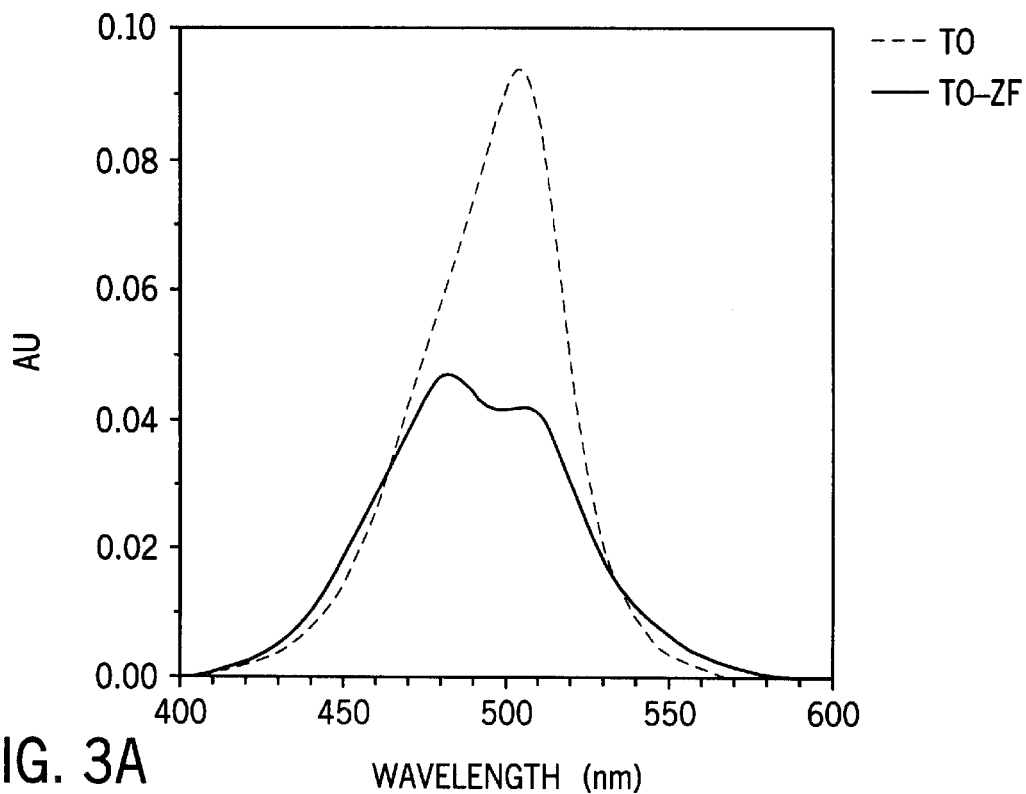
FIGS. 3A and 3B depict the absorbence spectra for the thiazole orange-zinc finger conjugate (TO-ZF) and unconjugated thiazole orange (TO) in the absence (3A) and presence (3B) of GRE1 sequence (see FIG. 2).
Figure 3B:
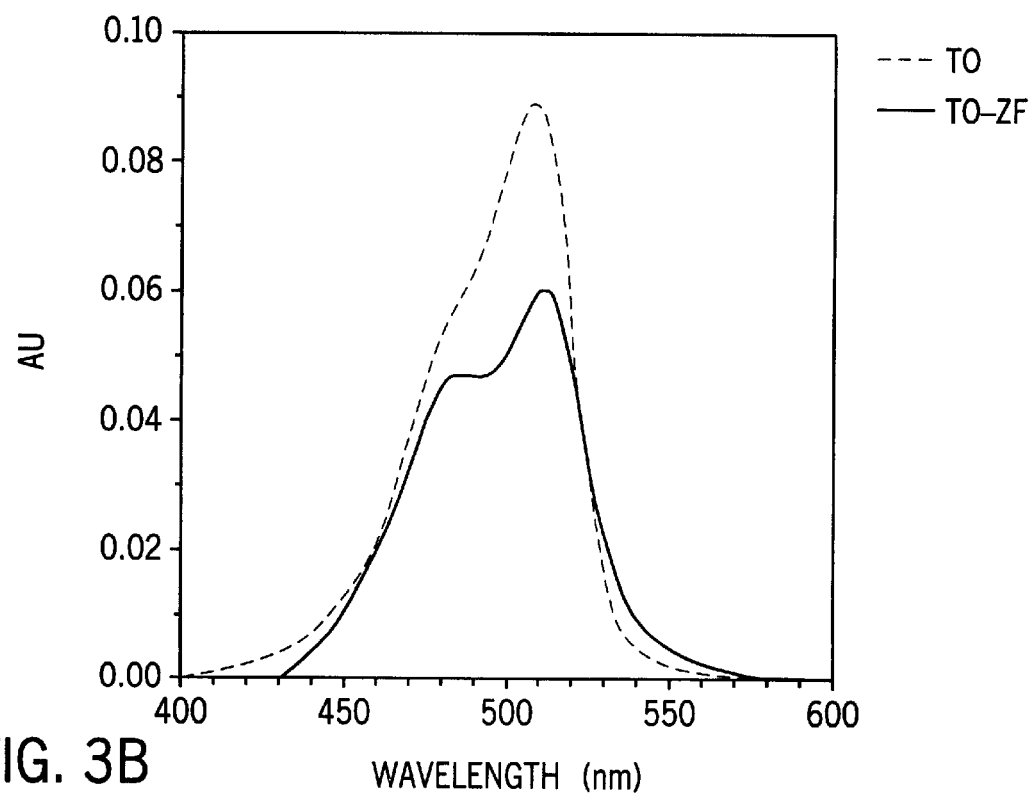

The UV-Visible spectrum of aqueous solutions of TO-ZF in the presence and absence of dsDNA are compared to that of the unconjugated thiazole orange molecule. FIG. 3 shows the absorbence spectra for the thiazole orange-zinc finger conjugate (TO-ZF) and unconjugated thiazole orange (TO) in 20 mM Tris (pH 7.9), 30 mM NaCl, 20 mM KCl, 1 mM $MgCl_2$, and 5% glycerol buffer in the absence and presence of 20 mM GRE1 sequence (see FIG. 2). Sample concentrations were 2 mM for TO-ZF and TO. TO-ZF was incubated 30 minutes with 2.5 mM $ZnCl_2$ prior to mixing with DNA. The TO and TO-ZF samples were incubated for 30 minutes with 20 mM GRE1 sequence. All spectra were corrected for dilutions made upon DNA addition. As shown in FIG. 3, the TO-ZF conjugate has two nearly equal absorbance maxima at 482 and 504 nm when coordinated with zinc or cadmium. In comparison, the absorbance maximum of unconjugated thiazole orange is at 503 nm with a much less prominent shoulder at 480 nm. After incubating the unconjugated thiazole orange with DNA for 30 minutes, the absorbance maxima redshifts from 503 nm to 510 nm. The redshift is due to thiazole orange intercalating into dsDNA. Similarly, the thiazole orange moiety of the TO-ZF conjugate shows a redshifted absorbance maxima as well when incubated with dsDNA. In this case the longer wavelength of the two absorbance transitions becomes more prominent and shifts from 504 nm to 511 nm.

Fluorescent dyes, such as fluorescein or rhodamine are known to exhibit subtle changes in their photophysical properties upon changes in solvent, pH or conjugation. D. C. Neckers, et al, *Adv. Photochem.* (1993). The spectrum changes exhibited by the thiazole orange molecule, as shown in FIG. 3, are more pronounced than those of most other dyes.

Figure 4A:
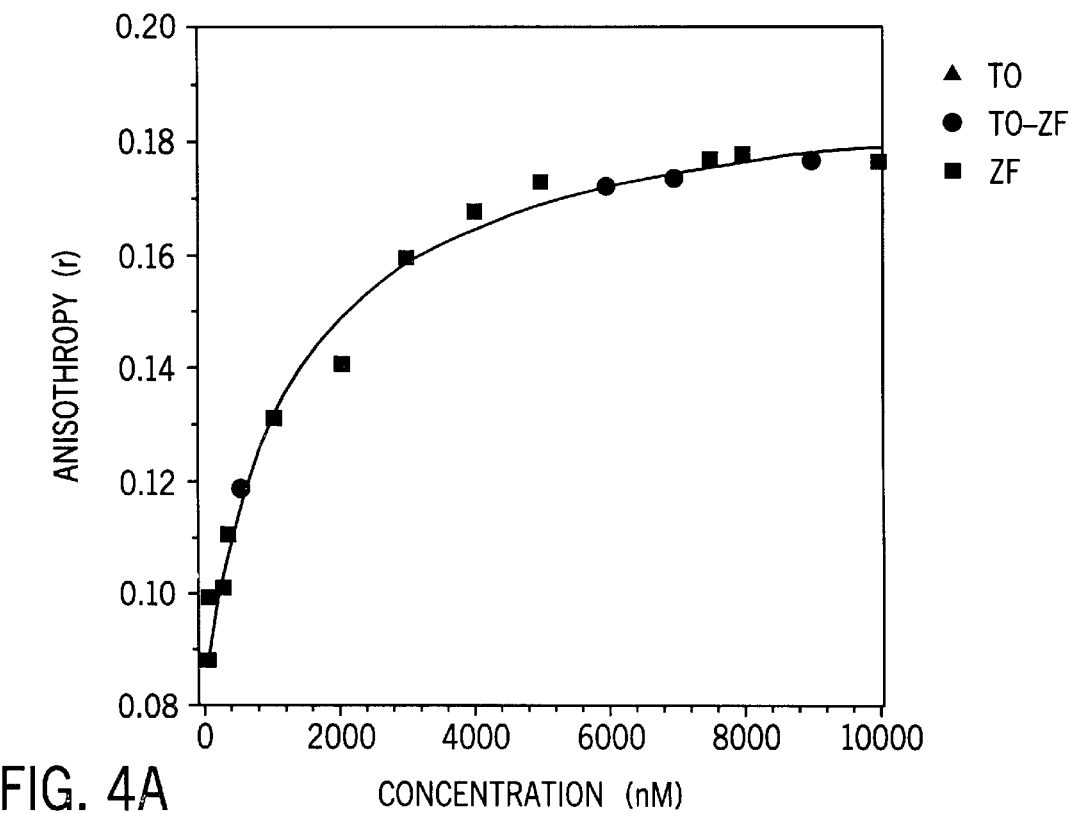
FIG. 4A depicts the fluorescence anisotropy measurement of 50 nM fluorescein labeled DNA titrated with the unconjugated zinc finger (ZF) binding protein (no TO attached).

Fluorescence changes upon binding of TO, ZF and TO-ZF to GRE containing duplex DNA. Equilibrium binding of the non-labeled zinc finger (ZF), unconjugated thiazole orange (TO) and thiazole orange-zinc finger conjugate (TO-ZF) to fluorescein labeled GRE2 sequence dsDNA was measured by both fluorescence anisotropy and total fluorescence. For these experiments, a fluorescein labeled GRE2 was used at either 50 nM (TO and ZF titrations) or 1 nM (TO-ZF titrations). For fluorescein fluorescence, excitation was at 491 nm and emission was detected at 521 nm. Each peptide sample was titrated into a constant concentration of fluorescein labeled DNA. Changes in the steady-state anisotropy of the fluorescein fluorescence from the labeled GRE sequence containing DNA (F-GRE2) can arise from two sources. Binding of the zinc finger to the DNA slows the rotational time of the DNA and thus decreases the depolarization in the steady state (increasing the anisotropy). Binding of the TO dye to the DNA can also decrease the excited state lifetime of the fluorescein due to energy transfer from fluorescein to TO. This again decreases the steady state depolarization of the dye (because the molecule does not rotate as much within the shorter excited state lifetime) and therefore increases the anisotropy. FIG. 4A shows the change in steady-state anisotropy upon binding of the sequence specific zinc finger to the GRE sequence containing dsDNA. The solid line in FIG. 4A represents a fit to equation 1 for the anisotropy of the zinc finger. The dissociation constant determined for ZF (not conjugated to TO) from a fit to equation 1 is 1.1 $\mu$M. By comparison, the amino acid zinc finger Xfin-31 was determined to have a dissociation constant of approximately 1 μM, M. S. Lee, et al., *FEBS* 279:289–294 (1991), whereas, the 66 amino acid zinc finger from GATA-1 has a dissociation constant of 10 nM. J. G. Omichinski, et al., *Proc. Nat. Acad. Sci. USA* 90:1676–1680 (1993). Similar anisotropy measurements were also taken for TO and the TO-ZF conjugate, but energy transfer between the fluorescein attached to the DNA and the TO (see below) complicates the interpretation of the anisotropy ratio.

Figure 4B:
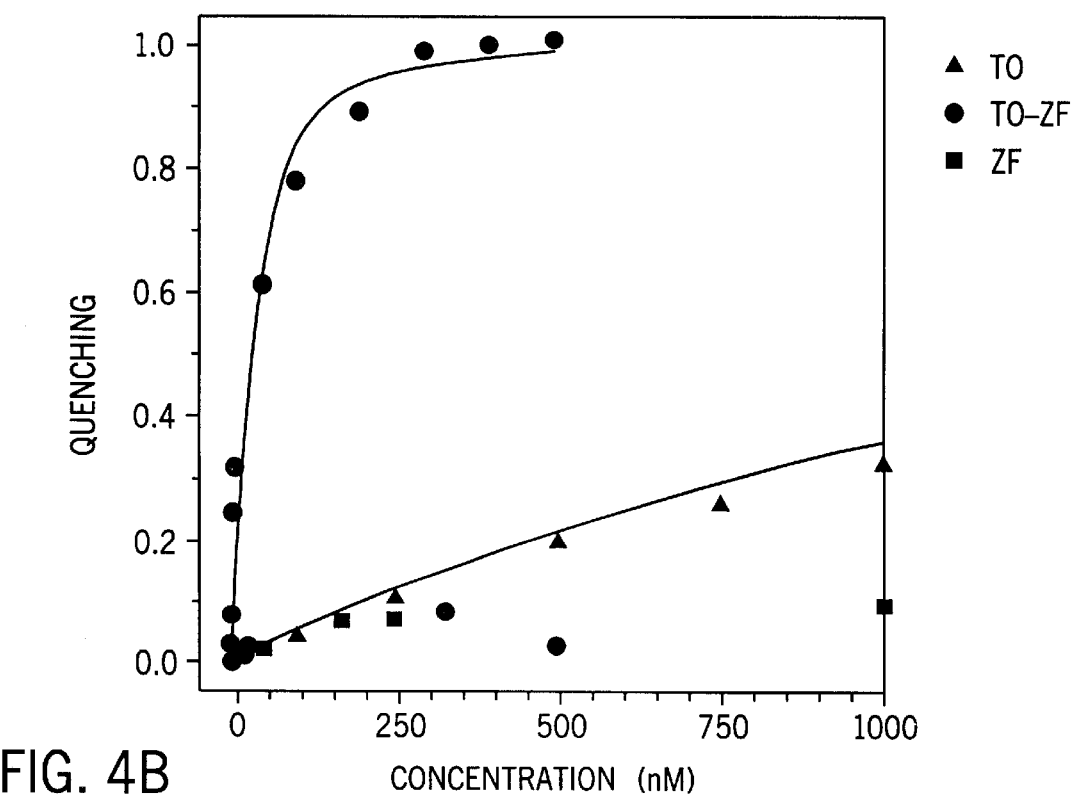
FIG. 4B depicts the total fluorescence quenching due to energy transfer upon titrating the TO-Zn conjugate with fluorescein labeled DNA (calculated as $[(F_{max}-F_i)/F_{max}]$, where $F_{max}$ is the fluorescence in the absence of titrant, and $F_i$ is the measured fluorescence during the titration).

Total fluorescence data, performed in parallel with the anisotropy measurements, are shown in FIG. 4B for ZF as well as for TO and the TO-ZF conjugate. Essentially no change is seen in the total fluorescence over the course of the titration, when the ZF itself binds to the fluorescein-labeled GRE2 DNA. In contrast, both the TO-ZF conjugate and the TO alone result in large decreases in steady state fluorescence. The decrease in fluorescence collected from fluorescein upon addition of TO or TO-ZF is due to energy transfer from fluorescein to thiazole orange. T. Forster, in *Modem Quantum Chemistry*, 93–137 (1965). Contributions to the fluorescence signal at 521 nm by thiazole orange were only a few percent of the maximum fluorescence detected and were corrected for by performing control runs with unlabeled DNA as described in the Methods section. In the case of the TO-ZF conjugate, the expected distance between the fluorescein and the intercalated thiazole orange is in the range of 20–30 angstroms. This distance range is short enough to allow efficient through-space energy transfer.

The solid lines in FIG. 4B represent a fit to equation 2 for the total fluorescence measurements. Fitting of the quenching curve (FIG. 4B) to a two-state binding model (see Materials and Methods) resulted in a dissociation constant for TO-ZF binding to the target GRE2 dsDNA binding sequence of 14 nM. The dissociation constant for the unconjugated TO was found to be two orders of magnitude higher at 2.4 μM. However, one must be careful about interpreting the quenching curve for unconjugated TO directly in terms of a binding constant, since TO binds to many different sites on the DNA and thus its position relative to the fluorescein is distributed, causing the fluorescence energy transfer efficiency to be heterogeneous in the sample. The TO binding constant can be estimated from binding curves in which the TO fluorescence is monitored directly, as described below.

Titrations of the TO fluorescence upon binding of TO-ZF to unlabeled DNA were measured for the dsDNA sequences shown in FIG. 2. TO fluorescence was excited at 510 nm and collected at 535 nm. The GRE1 DNA sequence contains the same binding site as does the GRE2 DNA sequence used above, however, the GRE3 sequence contains a single mutation of the guanine in the native GRE target sequence (5'-TGTTCT-3') to an adenine. The GRE2 and GRE3 sequences were generated for use in the photocleavage measurements described below. Finally, the GRE4 and ERE recognition sequences are from the non-specific GRE half-site and the estrogen response element (ERE), respectively. M. A. L. Eriksson, *J. Molec. Biol.* 253:453–472 (1995). These are used in conjunction with the other sequences to determine the sensitivity of this probe. The DNA is not fluorescently labeled in these measurements. Therefore, the fluorescence is exclusively from thiazole orange molecules intercalated into dsDNA.

Figure 5A:
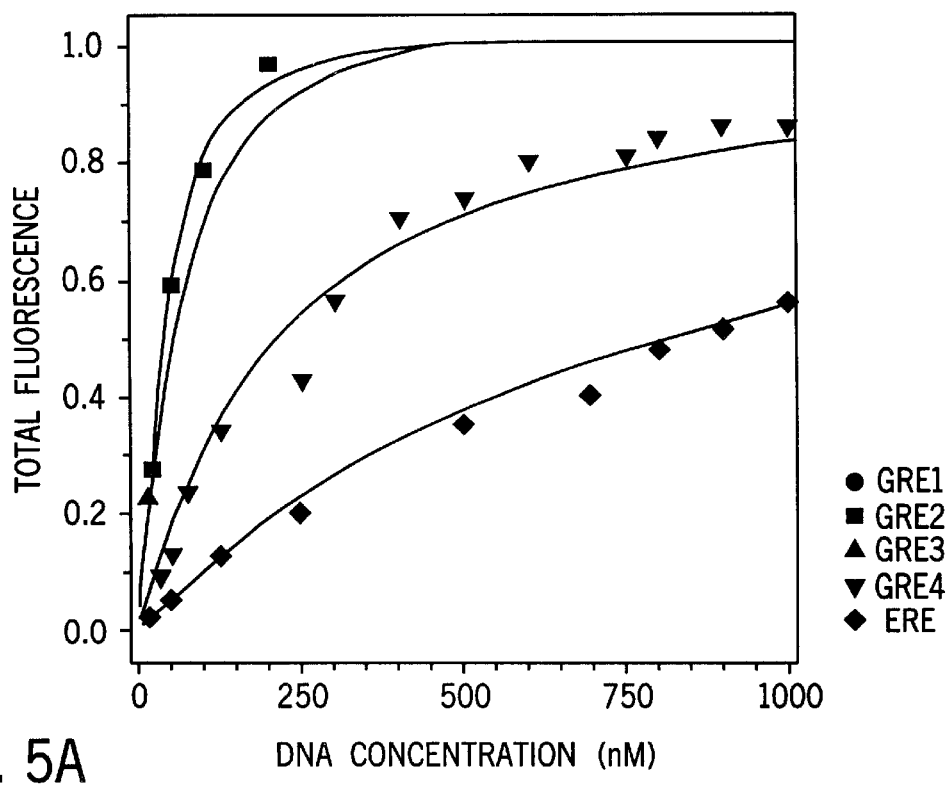
FIG. 5A are graphs of the comparison of total fluorescence (which is calculated as the sum of the parallel and 2 times the perpendicular fluorescence intensities) due to sequence specific and non-sequence specific bonding of TO-ZF when titrated with increasing concentrations of either GRE1, GRE2, GRE3, GRE4 or ERE dsDNA sequences (FIG. 2).

FIG. 5A shows the effect of altering the DNA sequence on the binding of TO-ZF (fluorescence measurements are given as a fraction of total fluorescence: $F_i/F_{max}$). Fitting the binding curves to a two-state binding model (see Materials and Methods) results in a dissociation constant of 25 nM for GRE1 and GRE2, which contain the native GRE. Titrations of the modified GRE sequences and the ERE sequence yielded binding constants of 57 nM, 220 nM and 810 nM for the TO-ZF conjugate bound to GRE3, GRE4, and ERE, respectively.

As expected, the GRE1 and GRE2 sequences, which have the same target sequence, have essentially identical dissociation constants, in good agreement with the value determined for TO-ZF binding to the GRE2 sequence by fluorescein quenching above. However, as shown in FIG. 5A, the TO-ZF conjugate binds a dsDNA sequence containing the native GRE target sequence approximately 30-fold more efficiently than the ERE target sequence (which contains two base changes relative to the GRE). More interestingly, the two different single base modifications within the native GRE sequence, GRE3 and GRE4, result in a 2-fold and a 10-fold increase in the dissociation constant relative to the native GRE, respectively. It should be noted that the modification in GRE3 is at the guanine where a base contact by the peptide was intentionally removed (used as the site of TO attachment) in the conjugate used here. Thus, this base change is expected to have only a small effect on binding, as observed. The base change in the GRE4 sequence, which is in the middle of the binding site for the zinc finger, shows a much larger effect on the dissociation constant (FIG. 5A). The GRE4 results indicate that the zinc finger is able to dictate the binding specificity of the TO-ZF conjugate well enough to discriminate between binding sites with single base changes, at least in the more sensitive region of the sequence.

Figure 5B:
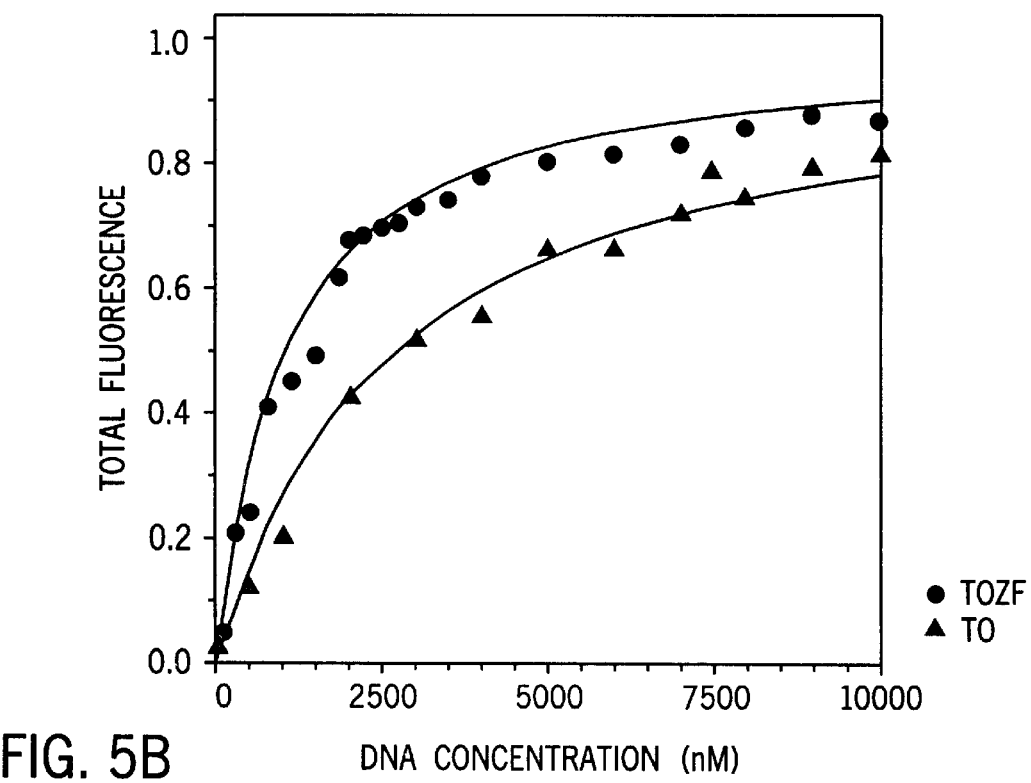
FIG. 5B graphs total fluorescence measurements of 50 nM TO-ZF or 50 nM unconjugated TO titrated with dsDNA [poly(dG)-poly(dC)] not containing the GRE target sequence.

The overall specificity of TO-ZF binding to dsDNA containing the native GRE target sequence was investigated by comparing the data of FIG. 5A to a titration of the TO-ZF conjugate with a dsDNA sequence that did not contain any target GRE sequence. FIG. 5B compares the binding of unconjugated thiazole orange and TO-ZF conjugate to a poly(dG)-poly(dC) 20-mer (fluorescence measurements are given as a fraction of total fluorescence ($F_i/F_{max}$) and the solid lines represent a best fit to equation 2). The contributions of the zinc finger towards non-specific binding give it slightly enhanced binding over the unconjugated thiazole orange. The dissociation constants for the unconjugated thiazole orange and TO-ZF conjugate are 2.4 μM and 1.1 μM, respectively. Previous studies of unconjugated thiazole orange, using a 5-fold higher salt concentration determined the dissociation constant for binding to dsDNA to be approximately 3 μM. J. Nygren, et al., *Biopolymers* 46:39–51 (1998). Parallel titrations with (dGdC)20 show, within experimental error, the same results as the poly(dG)-poly(dC) 20-mer. The dissociation constant of unconjugated thiazole orange is essentially independent of the sequence, as expected for a sequence neutral intercalating dye.

Footprinting of TO-ZF Conjugate. DNA footprinting by the TO-ZF conjugate was performed to determine if the TO-ZF conjugate was binding the same sequence as the native glucocorticoid receptor protein DNA-binding domain. More specifically, reaction samples (Maxam-Gilbert A+G and C+T sequencing reactions, radical hydroxyl cleavage of GRE2 in the presence of TO-ZF, radical hydroxyl cleavage of GRE2 in the absence of TO-ZF) contained 160 μM duplex DNA and 2.2 mM TO-ZF, 20 mM Tris (pH 7.9), 40 mM NaCl, 20 mM KCl, 1 mM MgCl2. The samples were incubated for 60 minutes in the dark at 25° C. The radical hydroxyl reaction proceeded for 60 seconds at 25° C. It is clear that the binding is localized within the native GRE target sequence. The bound TO-ZF complex protects a four base pair region (TTCT) within the native GRE binding sequence that correlates well with the location of the N-terminal zinc finger of native glucocorticoid receptor protein-DNA-binding domain that is shown in the crystal structure. (B. F. Luisi, et al., *Nature* 352:497–505, 1991) A control experiment performed in the absence of TO-ZF shows no protection in this region.

Photocleavage of TO-ZF conjugate. We examined the photoinduced cleavage of 5'-32P-end-labeled dsDNA fragments containing the dsDNA sequences GRE1, GRE2 and GRE3 in the presence of either unconjugated TO or TO-ZF. Note that the data shown is only of the photocleavage observed in the DNA strands displayed in FIG. 2. We have performed similar photocleavage measurements of the complementary strands in the dsDNA duplexes used in each case. However, the sequence-dependence of the observed photocleavage positions is apparently the same on both strands. Therefore, we have concentrated on the photocleavage observed in the strands shown (FIG. 2), while realizing that cleavage of the complementary strand is in all cases a competing reaction. After irradiation of TO-ZF bound to dsDNA in Tris buffer solution at 514 nm (514 nm is in the main band of the absorbance spectrum of intercalated thiazole orange as shown in FIG. 3), the photo-products were denatured and separated using denaturing polyacrylamide gel electrophoresis (PAGE). The unconjugated cyanine dyes oxazole yellow and thiazole orange have been shown previously to cause single stranded breaks in supercoiled DNA upon UV-visible irradiation. Irradiation of randomly intercalated thiazole orange at 514 nm leads to both alkali dependent and direct cleavage upon visible illumination. Piperidine treatment is a common method used to induce strand cleavage at basic sites or oxidized guanines formed during a photochemical reaction, whereas direct cleavage does not require piperidine treatment. (B. Armitage, *Chem. Rev.* 98:1171–1200,1998) The mechanism of strand cleavage is not entirely clear for either alkali dependent and direct cleavage. Like many fluorescent dyes, H. Morrison, et al., Photochemistry and Photobiology 66:245–252 (1997); E. Tuite, et al., *Journal of Photochemistry and Photobiology B-Biology* 21:103–124 (1993), TO is thought to sensitize singlet oxygen formation, but the results of the photocleavage experiments described below suggest this is not the dominant reaction mechanism of photocleavage mediated by TO-ZF.

The thiazole orange molecule can extend up to 14 angstroms from the peptide backbone, due to the nature of the linkage used, permitting it to extend over a range of 1–4 base pairs on the 5'-side of the GRE. Photocleavage of GRE1 by TO-ZF causes piperidine dependent cleavage to occur predominantly at the guanine within the GRE (5'-TGTTCT-3'). This was shown by using a radioactively end-labeled GRE1 dsDNA segment and irradiating this with light in the presence or absence of the TO-ZF conjugate. Gel electrophoresis of the resulting photoproducts showed predominantly a band at the position corresponding to the G in the GRE recognition sequence. This cleavage depends not only on light and the TO-ZF conjugate, but also on the presence of piperidine which acts a base in the cleavage reaction. Presumably electron transfer from the guanine to the excited singlet state of TO (possibly involving intermediate hole transfer) is the dominant excited state decay pathway when a close-by guanine is available. Note that one reaches the same conclusion by analyzing the photoproducts of the complementary strand of the GRE1 dsDNA fragment, which also shows cleavage at nearby guanines with a preference for the GG sequence located 7 base pairs from the GRE.

Figure 6:
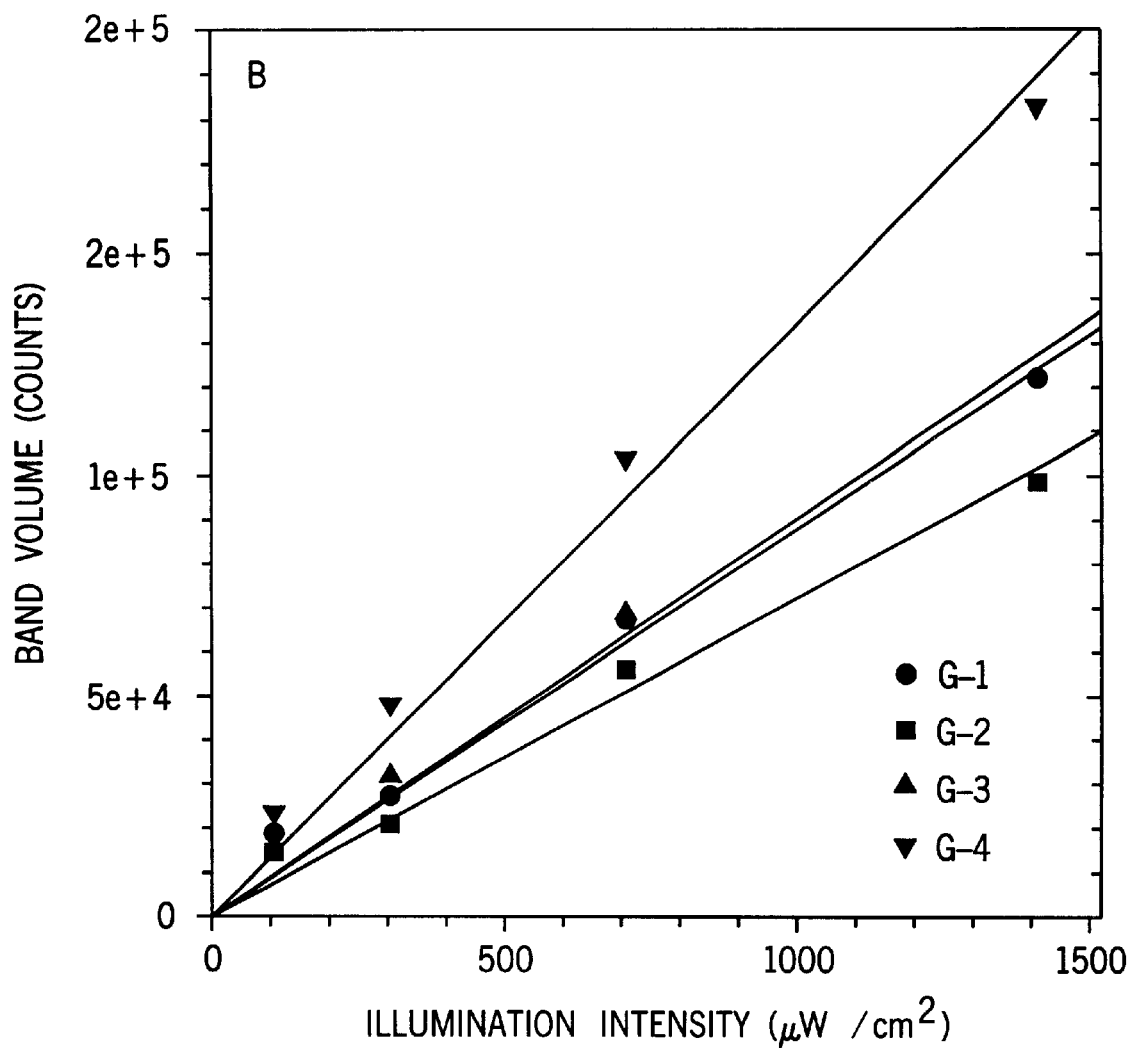
FIG. 6 is a graph of photocleavage of GRE2 by TO-ZF showing the intensity dependence of guanine oxidation. Plot showing the change in integrated band intensity with laser power for each observable guanine cleavage site.

Long range guanine oxidation, particularly at GG sequences, was explored more rigorously using the GRE2 dsDNA sequence (FIG. 2). The GRE2 sequence was designed to have a series of guanines both near and at some distance from the GRE target sequence, allowing for the possibility of long range hole transfer between guanines. Also, a GG site was introduced which is known to have a lower oxidation potential than a single G. M. A. Rodgers, et al., *J. Am. Chem. Soc.* 104:5541–5543 (1982). The experiment to show photocleavage of GRE2 by TO-ZF was done as the following: Reaction samples contained 160 nM duplex DNA and 200 nM TO-ZF in 20 mM Tris, pH 8.0. The samples were incubated for 15 minutes in the dark at 25° C. and irradiated at 514 nm for 5 minutes at intensities of 100, 300, 700 and 1500 mW/cm$^2$, respectively. All samples were reacted in the absence of oxygen and treated with piperidine. FIG. 6 shows that oxidation of remote guanines by excited state thiazole orange occurs over a range of 7 to 17 Å (17 Å was the farthest G in the DNA sequence used). A roughly linear increase in the product band formation at each guanine is observed as the intensity of the 514 nm argon ion laser was increased from 100 to 1400 mW/cm$^2$. Preferential cleavage is observed at the 5'-G of the GG sequence.

To explore other possible mechanisms of thiazole orange mediated photocleavage in the region on the 5'-side of the GRE target sequence, the guanine located within the GRE (5'-TGTTCT-3') in the GRE1 dsDNA fragment was changed to an adenine to give GRE3 (FIG. 2). In the GRE3 dsDNA fragment, there are no G's present on the strand shown (of course there are G's on the complementary strand which can and do undergo competing photochemistry, but these are invisible in the results displayed here because the complementary strand was not labeled). Fluorescence measurements of TO-ZF binding to GRE1 and GRE3 target sequences (FIG. 5A) show only a modest difference in the dissociation constant between the two sequences. Thus the measured changes in the photocleavage products between GRE1 and GRE3 are not an artifact of strong differences in the binding affinity of TO-ZF between these sequences. Photo-induced cleavage of the GRE3 sequence by TO-ZF assayed by gel electrophoresis shows a confined group of bands flanking the altered GRE sequence which are only partially piperidine dependent. The total chemical yield of the piperidine dependent reactions in these bands, measured as the number of fluorescence counts in product bands divided by the total counts of a given lane, increased three-fold from 2% in GRE1 (described above) to 6% in GRE3 for samples reacted in the presence of oxygen. Piperidine treated samples reacted in the absence of oxygen showed a 10–20% lower chemical yield.

A comparison of the band patterns observed in the photocleavage products for GRE1 and GRE3 show that when a guanine is nearby, guanine oxidation and cleavage is the only photochemistry observed above background. In the absence of a local guanine, the location of the major bands are 2 and 3 bases from the 5' end of the GRE under all photocleavage conditions described. Note that in the GRE3 sequence, the GG pair which is present on the complementary strand in GRE1 is not present and thus cannot act as a trap for hole migration. Independent experiments in which the complementary strand was labeled show that the other G's present on the complementary strand to GRE3 do act as electron donors and undoubtedly compete with direct photocleavage of the strand shown in FIG. 2.

The role of singlet oxygen as a reactive intermediate was probed by using $D_2O$ rather than $H_2O$ in the buffer of parallel samples. Deuterium oxide increases the lifetime of singlet oxygen and therefore, if singlet oxygen is created by excitation of the dye, its potential to cause damage will increase proportionally. H. Sugiyama, et al., *J. Am. Chem.*

Soc. 118:7063–7068 (1996). However, in these experiments, strand cleavage shows at most there is a 25% increase in band intensity in the presence of $D_2O$. This coupled with the small (10–20%) effects of removing oxygen imply that singlet oxygen mediated cleavage plays at most a minor role.

EXAMPLE 2—HTH/TO AND HTH/YO CONJUGATES

Methods

Materials. Lepidine, 5-bromovaleric acid, 3-methylbenzothiazole-2-thione, 2-mer captobenzoxazole, para-toluenesulfonate, iodomethane, anhydrous ethanol, and triethylamine were purchased from Aldrich and used without further purification. F-moc amino acids and peptide synthesis reagents were purchased from Advanced Chemtech. The F-moc-Lys (Mtt)-OH was purchased from Anaspec.

Instrumentation. Peptides were synthesized on a Millipore 9050 peptide synthesizer. Purification of synthetic peptides was performed on an HPLC. Absorbance measurements were made on a Cary V spectrophotometer. Steady-state fluorescence and fluorescence anisotropy measurements were performed on a Spex fluorometer.

Labeled and nonlabeled peptide synthesis, purification and characterization. The cyanine dyes coupled to the DNA-binding domains were synthesized as described previously. H. Rye, et al., supra, 1992; M. Thompson, et al., *Biochemistry*. 39:4327–4338 (2000). Labeled and unlabeled peptides were synthesized on PAL-PEG-PS resin by automated solid-phase peptide synthesis using F-moc chemistry, S. B. H. Kent, supra, 1988, as described previously. M. Thompson, et al., supra, 2000.

The peptides were purified by RP-HPLC on a Zorbax C8 column (9.4 mm×25 cm) using a water (0.1% TFA)—acetonitrile (0.1% TFA) gradient. Identities of the peptides were confirmed by amino acid analysis and matrix-assisted laser desorption ionization-time of flight (MALDI-TOF) mass spectrometry. Stock solution concentrations of both the nonlabeled and labeled peptide were determined spectrophotometrically. The extinction coefficient $e_{280nm}$=4200 $M^{-1}$ $cm^{-1}$ calculated for tyrosine absorption, C. R. Cantor, et al., *Conform. Biol. Macromol.* (1980), was used for nonlabeled peptides. For the dye labeled peptides, concentrations were determined from the extinction coefficients of e280 nm=40,500 $M^{-1}$ $cm^{-1}$ for YOH in and e280 nm=50, 800 $M^{-1}$ $cm^{-1}$ for TOTc3.

DNA Synthesis and Purification. All oligonucleotides were synthesized on a DNA synthesizer using phosphoramidite chemistry, M. H. Caruthers, et al., *Meth. Enzymol.* 154:287–313 (1987), and purified on a 15% denaturing polyacrylamide gel. Bands were cut out and recovered by soaking the crushed gel pieces in 100 mM Tris, (pH 8.0) 100 mM NaCl buffer for 4–6 hours. Extractions were combined and the urea and salts removed by spin filtration or a Sephadex G-15 size exclusion column. Concentrations for purified single stranded oligonucleotides were calculated using the nearest neighbor method, E. F. Fritsch, et al., *Molecular cloning: A laboratory manual*, 1146 (1989); J. C. Kendrew, et al., *The Encyclopedia of Molecular Biology*, In *Hybridization*, 503–506 (1994), except for the tetramethylrhodamine labeled labeled strands which were determined spectrophotometrically by using e542 nm=81,000 $M^{-1}$ $cm^{-1}$. R. P. Haugland, supra, 1996. Nonlabeled strands for use with reverse titrations of the conjugates were annealed using the same molar equivalent of each oligonucleotide. Each tetramethylrhodamine labeled oligo was annealed with 1.5 molar equivalents of its unlabeled complement. The excess single stranded DNA is not expected to alter the results because monomeric cyanine dyes do not bind the single stranded DNA. The oligonucleotides used in this study are shown in FIG. 8.

Fluorescence Measurements. Steady state fluorescence anisotropy and total fluorescence measurements were performed as forward and reverse titrations, respectively, as described previously, M. Thompson, et al., supra, 2000. Forward titrations of the tetramethylrhodamine labeled DNA (TMR-DNA) with nonlabeled DNA-binding domains were performed at 10 nM TMR-DNA. Vertical excitation was at 542 nm with detection in the verticle and horizontal planes at 582 nm. Reverse titrations of 1 nM of the appropriate conjugate were titrated with nonlabeled DNA. Excitation and emission detection was at 480 nm and 510 nm for oxazole yellow and 510 nm and 535 nm for thiazole orange samples. Salt dependence studies were performed by titrating an appropriate amount of 1 M NaCl in the same Tris buffer to yield the indicated final salt concentration. Temperature dependence studies were performed by incubating each sample for 30 minutes at the given temperature. The temperature of the sample was held constant by pumping water through the cuvette holder from a temperature equilibrated water bath. Each titration was performed at least 3 times.

Determination of thermodynamic functions. The contribution of the hydrophobic effect and the polyelectrolyte effect to the stability of the conjugate or DNA-binding domain—DNA complex is assessed by analysis of the dependence of the observed association equilibrium constant Kobs for a range of temperatures and salt concentrations as in the following:

$$K_{obs} = \frac{[PD]_{eq}}{[P]_{eq}[D]_{eq}}$$

where, [P] eq is the concentration of the conjugate or DNA-binding domain, [D] eq is the concentration of DNA, and [PD] eq is the concentration of bound complex at equilibrium. The analysis is based on the assumption that this is a single-step bimolecular reaction.

Here, the stability of the bound complex is determined by the differences in the non-covalent interactions between the peptide and the DNA as salt concentration and temperature are varied.

Results

Figure 7:
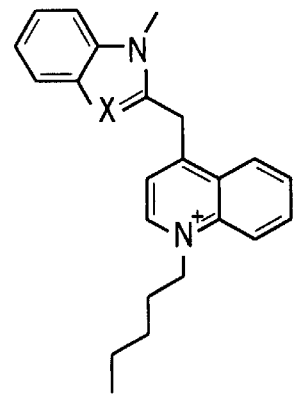
FIG. 7 is a schematic representation comparing primary and secondary structure of the thiazole orange-Tc3 transposase DNA binding domain (TOTc3) and the oxazole yellow-Hin recombinase DNA binding domain (YOHin) conjugates.

Characterization of the conjugates. FIG. 7 shows schematic representations comparing primary and secondary structure of the thiazole orange-Tc3 transposase (TOTc3) and the oxazole yellow-Hin recombinase (YOHin) conjugates. The 52 amino acid Tc3 DNA-binding domain tethered to the dye was derived from residues 202–253 of the native Tc3 transposase and the 52 amino acid Hin DNA-binding domain tethered to the dye was derived from residues 139–190 of the native Hin recombinase. In FIG. 7, the location of the appropriate cyanine dye is shown in brackets and the underlined residues are those having a-helical secondary structure. The purified 52 amino acid TOTc3 conjugate (thiazole orange conjugated to the Tc3 DNA binding domain) was characterized using matrix-assisted laser desorption ionization-time of flight (MALDI-TOF) mass spectrometry. The expected mass of TOTc3 is 6209.8 and a sharp peak in its mass spectrum is observed for the singly charged species at (m/e)=6210.9. By comparison, the expected mass of the Tc3 DNA-binding domain itself is 5843.8 and a sharp peak in its spectrum is observed for the singly charged species at (m/e)=5841.0. The expected mass of the purified 52 amino acid YOHin conjugate (oxazole yellow conjugated to the Hin DNA binding domain) is 6522,3 and a sharp peak in its mass spectrum is observed for the singly charged species at (m/e)=6523.8. By comparison, the expected mass of the Hin DNA-binding domain itself is 6163.2 and a sharp peak in its spectrum is observed for the singly charged species at (m/e)=6160.9. The conjugate was further characterized by reversed phase HPLC. An HPLC analysis of purified conjugates and unlabeled peptides shows only one peak in the chromatograph, which confirms the purity of these preparations.

Specific binding by the dye labeled peptides (conjugates). The binding affinity of the two dye labeled peptides comprising the Hin recombinase and Tc3 transposase DNA-binding domains conjugated to oxazole yellow and thiazole orange, respectively, were determined. In this case, the total fluorescence intensity can be used to determine the binding affinity by these systems. Fluorescence intensity is superior to fluorescence anisotropy to determine the equilibrium binding constant of the conjugate because energy transfer between the bound intercalating dye and the label on the DNA used in the anisotropy measurements interferes with the anisotropy measurement. In addition, the bound and free populations of the conjugate, and therefore the dye, present at equilibrium have such an extreme increase in quantum yield (~1000–5000-fold) that the total fluorescence from the system is a very sensitive and accurate way to monitor binding. The oligonucleotides used for the binding assays are given in FIG. 8. Note that each oligonucleotide shown was hybridized to its conjugate forming a dsDNA segment.

Figure 9A:
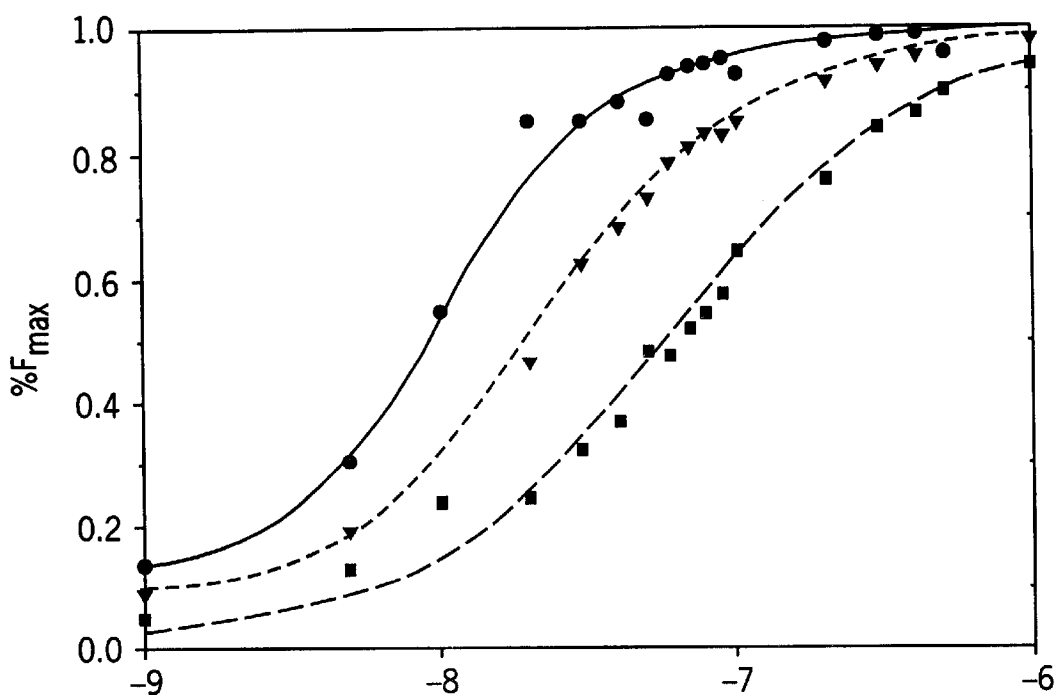
FIGS. 9A and FIG. 9B are graphs of representative binding curves derived from titrations of the conjugates YOHin FIG. 9A and TOTc3 FIG. 9B with their respective consensus sequences as a function fo salt concentration and temperature.
Figure 9B:
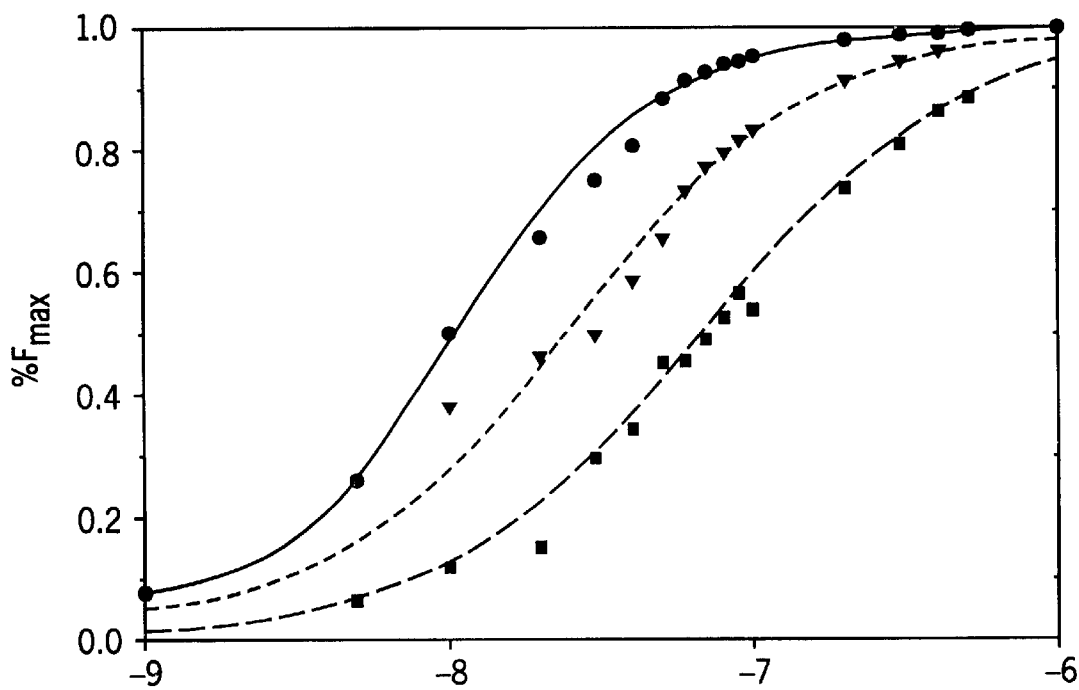

FIG. 9 shows representative binding data determined by total fluorescence counts from the oxazole yellow-Hin recombinase (YOHin) DNA-binding domain and thiazole orange-Tc3 transposase (TOTc3) DNA-binding domain conjugates as a function of the concentration of the native consensus sequence for the YOHin (FIG. 9A) or TOTc3 (FIG. 9B) conjugate, respectively. In FIG. 9, semi-log plot of the total fluorescence of I nM conjugate is plotted as the log of the concentration of nonlabeled DNA containing each respective consensus sequence. The solid lines represent a fit for the percent of the maximal fluorescence values at 298 K, 0.150 M Na+, (●),313 K, 0.150 M Na+ (t) and 298 K, 0.250 M Na+(■). The binding constants ($K_{obs}$) determined from these curves and the corresponding binding free energies (DG°) are given in Table 1 for the range of salt concentrations (0.15 to 0.25 M Na+) and temperatures (275 to 313 K) investigated. The equilibrium constant decreases 7- and 10-fold for the TOTc3 and YOHin, respectively, when the salt concentration is increased from 0.15 to 0.25 M salt. These data are summarized in Table 1.

TABLE 1

The equilibriam constants ($K_{obs}$) determined for sequence specific interactions of YOHin and TOTc3 conjugates.

| Temp (K) | [Na$^+$] (M) | $K_{obs}$ ($M^{-1}$) × $10^{-6}$ | $\Delta G°$ (kcal/mol) |
|---|---|---|---|
| YOHin conjugate | | | |
| 275 | 0.150 | 22 | −9.2 |
| 278 | 0.150 | 21 | −9.3 |
| 283 | 0.150 | 40 | −9.8 |
| 288 | 0.150 | 61 | −10.3 |
| 293 | 0.150 | 143 | −10.9 |
| 298 | 0.150 | 83 | −10.8 |
| 303 | 0.150 | 60 | −10.8 |
| 308 | 0.150 | 41 | −10.7 |
| 313 | 0.150 | 29 | −10.7 |
| 298 | 0.175 | 67 | −10.7 |
| 298 | 0.200 | 37 | −10.3 |
| 298 | 0.225 | 29 | −10.2 |
| 298 | 0.250 | 14 | −9.8 |
| TOTc3 conjugate | | | |
| 275 | 0.150 | 22 | −9.2 |
| 278 | 0.150 | 26 | −9.4 |
| 283 | 0.150 | 40 | −9.8 |
| 288 | 0.150 | 21 | −9.6 |
| 293 | 0.150 | 66 | −11.5 |
| 298 | 0.150 | 245 | −10.4 |
| 303 | 0.150 | 49 | −10.7 |
| 308 | 0.150 | 22 | −10.4 |
| 313 | 0.150 | 22 | −10.5 |
| 298 | 0.175 | 83 | −10.8 |
| 298 | 0.200 | 40 | −10.4 |
| 298 | 0.225 | 26 | −10.1 |
| 298 | 0.250 | 17 | −9.9 |

We claim:

1. A method of identifying the presence or absence of a DNA molecule that contains a specific DNA sequence, comprising the steps of:
   (a) mixing a test sample with a peptide/dye conjugate comprising a covalently linked peptide and a dye, wherein the peptide binds to the specific DNA sequence and wherein the peptide/ dye conjugate will fluoresce only if the peptide is bound to the specific DNA sequence; and
   (b) measuring fluorescence, wherein specific fluorescence above background level indicates that the conjugate is bound to the specific DNA sequence.

2. The method of claim 1, wherein the dye is a cyanine dye.

3. The method of claim 1, wherein the dye is selected from the group consisting of cyanine, phenanthridine and acridine dyes.

4. The method of claim 3, wherein the dye is oxazole yellow or thiozole orange.

5. The method of claim 1, wherein the peptide is a zinc finger.

6. The method of claim 1, wherein the peptide is a glucocorticoid receptor DNA binding domain zinc finger.

7. The method of claim 6, wherein the specific DNA sequence is a glucocorticoid receptor response element.

8. The method of claim 1, wherein the peptide is a helix-turn-helix motif.

9. The method of claim 1, wherein the peptide is a Tc3 transposase DNA binding domain helix-turn-helix motif.

10. The method of claim 9, wherein the specific DNA sequence is the Tc3 transposase DNA binding domain native consensus sequence.

11. The method of claim 1, wherein the peptide is a Hin recombinase DNA binding domain helix-turn-helix motif.

12. The method of claim 11, wherein the specific DNA sequence is the Hin recombinase DNA binding domain native consensus sequence.

13. The method of claim 1 further comprising the step of administering light to the conjugate after the conjugate has bound to the DNA sequence such that cleavage of the DNA results.

14. The method of claim 13, wherein the dye is selected from the group consisting of cyanine, phenanthridine and acridine dyes.

15. A peptide/dye conjugate comprising:
   (a) a peptide that binds to a specific DNA sequence; and
   (b) a dye capable of fluorescence only when the conjugate is bound to a specific DNA sequence, wherein the dye is covalently linked to the peptide.

16. The conjugate of claim 15, wherein the dye is selected from the group consisting of thiazole orange and oxazole yellow.

17. The conjugate of claim 15, wherein the dye is a cyanine dye.

18. The conjugate of claim 17, wherein the cyanine dye is oxazole yellow or thiozole orange.

19. The conjugate of claim 15, wherein the peptide is a zinc finger.

20. The conjugate of claim 15, wherein the peptide is a glucocorticoid receptor DNA binding domain zinc finger.

21. The conjugate of claim 20, wherein the peptide binds specifically to a glucocorticoid response element.

22. The conjugate of claim 20, wherein the dye is thiazole orange.

23. The conjugate of claim 15, wherein the peptide is a helix-turn-helix motif.

24. The conjugate of claim 15, wherein the peptide is a Tc3 transposase DNA binding domain helix-turn-helix motif.

25. The conjugate of claim 15, wherein the specific DNA sequence is the Hin recombinase DNA binding domain native consensus sequence.

26. The conjugate of claim 24, wherein the peptide binds specifically to the Tc3 transposase DNA binding domain native consensus sequence.

* * * * *

SEQUENCE LISTING

<160> NUMBER OF SEQ ID NOS: 12

<210> SEQ ID NO 1
<211> LENGTH: 28
<212> TYPE: PRT
<213> ORGANISM: Artificial Sequence
<220> FEATURE:
<223> OTHER INFORMATION: Description of Artificial Sequence:Zinc Finger -continued

```
<400> SEQUENCE: 1

Lys Leu Cys Leu Val Cys Ser Asp Glu Ala Ser Gly Cys Arg Tyr Gly
 1               5                  10                  15
Val Leu Thr Cys Gly Ser Cys Lys Val Phe Phe Lys
            20                  25

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence:GRE

<400> SEQUENCE: 2
tcataccact aactgttcta tca                                          23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:GRE

<400> SEQUENCE: 3
tgatacggct gactgttcta tga                                          23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:GRE

<400> SEQUENCE: 4
tcatacatct aactattcta tca                                          23

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:GRE

<400> SEQUENCE: 5
tcatacatct aactgtccta tca                                          23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:ERE

<400> SEQUENCE: 6
tcatacatct aactgaccta tca                                          23

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:GRE

<400> SEQUENCE: 7
tacggctgac tgttctatga                                              20
```

<210> SEQ ID NO 8
<211> LENGTH: 51
<212> TYPE: PRT
<213> ORGANISM: Artificial Sequence
<220> FEATURE:
<223> OTHER INFORMATION: Description of Artificial Sequence:HTH

<400> SEQUENCE: 8

Pro Arg Gly Ser Ala Leu Ser Asp Thr Glu Arg Ala Gln Leu Asp Val
 1               5                  10                  15

Met Lys Leu Leu Asn Val Ser Leu His Glu Met Ser Arg Lys Ile Ser
            20                  25                  30

Arg Ser Arg His Cys Ile Arg Val Tyr Leu Lys Asp Pro Val Ser Tyr
        35                  40                  45

Gly Thr Ser
    50

<210> SEQ ID NO 9
<211> LENGTH: 52
<212> TYPE: PRT
<213> ORGANISM: Artificial Sequence
<220> FEATURE:
<223> OTHER INFORMATION: Description of Artificial Sequence:HTH

<400> SEQUENCE: 9

Gly Arg Pro Arg Ala Ile Asn Lys His Glu Gln Glu Gln Ile Ser Arg
 1               5                  10                  15

Leu Leu Glu Lys Gly His Pro Arg Gln Gln Leu Ala Ile Ile Phe Gly
            20                  25                  30

Ile Gly Val Ser Thr Leu Tyr Arg Tyr Phe Pro Ala Ser Ser Ile Lys
        35                  40                  45

Lys Arg Met Asn
    50

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
atcggcacga tgctagttct ataggacccc cc                                    32

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
tcttatcaaa aacactatcg tcgcacggct ac                                    32

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence:
      oligonucleotide -continued

```
<400> SEQUENCE: 12
tccatgcacg tcgacgtacg tcgcacggct ac                                32
```